(12) United States Patent
Moeskops et al.

(10) Patent No.: US 10,398,506 B2
(45) Date of Patent: Sep. 3, 2019

(54) DEVICE FOR CUTTING HAIR (71) Applicant: KONINKLIJKE PHILIPS N.V., Eindhoven (NL)

(72) Inventors: Bastiaan Wilhelmus Maria Moeskops, Eindhoven (NL); Mark Thomas Johnson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 15/027,512

(22) PCT Filed: Sep. 25, 2014

(86) PCT No.: PCT/EP2014/070420
§ 371 (c)(1),
(2) Date: Apr. 6, 2016

(87) PCT Pub. No.: WO2015/051999
PCT Pub. Date: Apr. 16, 2015

(65) Prior Publication Data
US 2016/0242848 A1   Aug. 25, 2016

(30) Foreign Application Priority Data
Oct. 8, 2013   (EP) ..................................... 13187692

(51) Int. Cl.
*A61B 18/20* (2006.01)
*A61B 18/00* (2006.01)
(Continued)

(52) U.S. Cl.
CPC .. *A61B 18/203* (2013.01); *A61B 2017/00066* (2013.01); *A61B 2018/00476* (2013.01);
(Continued)

(58) Field of Classification Search
CPC ............ A61B 18/203; A61B 2090/034; A61B 2090/065; A61B 2017/00066;
(Continued)

(56) References Cited

U.S. PATENT DOCUMENTS 5,993,440 A    11/1999   Ghassemi
8,523,849 B2    9/2013   Liu
(Continued)

FOREIGN PATENT DOCUMENTS

EP    2189129 A1    5/2010
GB    2494248 A     4/2013
(Continued)

*Primary Examiner* — Michael W Kahelin
*Assistant Examiner* — Vynn V Huh (57) ABSTRACT

The present application relates to a device for cutting hair (1). The device has a skin contacting face (3) that is arranged to be placed against a surface of the skin (6) of a user during use, and an optical system configured to direct a cutting laser beam (8) across a cutting zone (5) parallel to and spaced from said skin contacting face (3) to cut hairs extending into the cutting zone (5). The device also has a skin sensor (18) configured to detect one or more optical properties of the surface of the skin (6), and a control unit (20) configured to adjust one or more characteristics of the optical system in dependence on the one or more optical properties of the skin (6) detected by the skin sensor (18). The present application also relates to a system for cutting hair comprising a device for cutting hair and a base unit for receiving the device.

7 Claims, 3 Drawing Sheets

(51) Int. Cl.
*A61B 17/00* (2006.01)
*A61B 90/00* (2016.01)

(52) U.S. Cl.
CPC ............... *A61B 2018/00702* (2013.01); *A61B 2018/00785* (2013.01); *A61B 2018/202* (2013.01); *A61B 2018/2023* (2017.05); *A61B 2018/20361* (2017.05); *A61B 2090/034* (2016.02); *A61B 2090/065* (2016.02)

(58) Field of Classification Search
CPC ............................. A61B 2018/00476; A61B 2018/00702; A61B 2018/00785; A61B 2018/202
USPC .................................... 606/2–14; 607/88–94
See application file for complete search history.

(56) References Cited

U.S. PATENT DOCUMENTS

| 2002/0049432 | A1 | 4/2002 | Mukai | |
| 2007/0208395 | A1* | 9/2007 | Leclerc | A61N 5/0616 607/86 |
| 2009/0270848 | A1* | 10/2009 | Weckwerth | A61N 5/0616 606/9 |
| 2012/0120375 | A1* | 5/2012 | Kilcher | G01S 7/4814 353/98 |
| 2012/0265182 | A1 | 10/2012 | Jay | |
| 2014/0074193 | A1* | 3/2014 | Luzon | A61B 5/44 607/89 |

FOREIGN PATENT DOCUMENTS

| WO | 199216338 A1 | 10/1992 |
| WO | 199533600 A1 | 12/1995 |
| WO | 2004010884 A1 | 2/2004 |
| WO | 2005102201 A1 | 11/2005 |

* cited by examiner

DEVICE FOR CUTTING HAIR

This application is the U.S. National Phase application under 35 U.S.C. § 371 of International Application No. PCT/EP2014/070420, filed on Sep. 25, 2014, which claims the benefit of International Application No. 13187692.2 filed on Oct. 8, 2013. These applications are hereby incorporated by reference herein.

FIELD OF THE INVENTION

The present invention relates to a device for cutting hair using a laser beam. The present invention also relates to a system for cutting hair comprising a device for cutting hair and a base unit for receiving the device.

BACKGROUND OF THE INVENTION

It is known to use a laser beam to sever hair as an alternative to an arrangement of mechanical cutting blades. Hair exposed to a laser beam will absorb energy from the laser beam and the hair will either be severed by vaporisation or by laser induced optical breakdown and a resulting shockwave. A laser beam requires no moving parts and so the problem of cutting elements becoming worn or blunt is eliminated. Moreover, use of a laser beam to sever hair avoids skin irritation caused by the sharp edges of mechanical blades contacting the skin. It is known from WO1992/16,338 and U.S. Pat. No. 5,993,440 to provide a device including a laser diode and reflective elements that direct a laser beam across a cutting zone so that the beam is substantially parallel to and spaced from the surface of the user's skin during use. In this way, as the device is moved across the skin, hairs that enter the cutting zone are exposed to the laser beam and severed at the point of interaction between the laser beam and the hair.

Shaving performance is typically measured by two criteria—closeness of shave and irritation of the skin. The cutting height is the distance between the surface of the skin and the point at which hairs are cut. A good performing shaver should minimise the cutting height and therefore minimise the remaining hair length by cutting the hairs as close as possible to the skin. However, positioning a laser beam close to the skin may cause skin irritation if heat and energy from the laser is incident on the skin. It is therefore necessary to protect the skin from a laser beam to avoid causing damage or irritation to the skin.

It is known that sensations and potential side-effects due to hair removal using a laser beam, for example skin irritation, may vary from user to user depending on skin type, sun exposure, and between different ethnic groups.

SUMMARY OF THE INVENTION

It is an object of the invention to provide a device for cutting hair using a laser beam and/or a system for cutting hair which substantially alleviates or overcomes the problems mentioned above.

According to the present invention, there is provided a device for cutting hair comprising a skin contacting face that is arranged to be placed against a surface of the skin of a user during use, an optical system configured to direct a cutting laser beam across a cutting zone parallel to and spaced from said skin contacting face to cut hairs extending into the cutting zone, a skin sensor configured to detect one or more optical properties of the surface of the skin, and a control unit configured to adjust one or more characteristics of the optical system in dependence on one or more of the optical properties of the skin detected by the skin sensor.

With this arrangement it is possible to minimise irritation of the skin by changing one or more characteristics of the optical system to reduce the effect of the laser beam inadvertently being incident on a user's skin dependent on one or more of the optical properties of the surface of the skin detected by the skin sensor.

Different skin types may be identified according to colour by use of the Fitzpatrick scale, in which skin type is identified in one of six types, between Type I which is identified as light, pale white and Type VI which is identified as black, very dark brown to black.

It has been determined that a device for cutting hair using a laser beam will, for a fixed laser parameter, give a different effect on skin of users having different skin colour. For example, it has been determined that the laser energy required to induce moderate skin damage, which is defined as local blistering, for Type II skin is around three times greater than the laser energy required to induce moderate skin damage for Type IV skin.

Therefore, by determining one or more optical qualities of the skin or the user it is possible to minimise any detrimental effects of the laser beam inadvertently being incident on a user's skin whilst maximising the shaving performance. Therefore, a uniform shaving performance can be maintained and variations in skin type can be accommodated by adjusting one or more characteristics of the optical system. Skin irritation may be reduced because operation of the cutting laser beam will be adjusted by one or more characteristics of the optical system in response to changes in one or more optical properties of the skin in the cutting zone.

The control unit may be configured to adjust the distance between the cutting laser beam and the skin contacting face in dependence on one or more of the optical properties of the skin detected by the skin sensor. Such an arrangement aims to adjust the distance between the cutting laser beam and the surface of the skin of a user.

With this arrangement it is possible to minimise the likelihood of the user's skin being incident with the cutting laser beam by adjusting the distance between the skin of a user and the cutting laser beam. Skin irritation will be reduced because the cutting laser beam will move relative to the skin in response to detected changes in the optical properties of the skin in the cutting zone and so the minimum distance between the cutting laser beam and the skin will change.

The device may further comprise a laser positioning mechanism arranged so that, when the device is in use, the distance between the cutting laser beam and said skin contacting face is adjustable to change the distance between the cutting laser beam and the surface of the skin of a user, and wherein the control unit is configured to operate the laser positioning mechanism in dependence on one or more of the optical properties detected by the skin sensor. The device may adjust the distance between the cutting laser beam and said skin contacting face at discrete time intervals, for example at least once during use, or continuously throughout use of the device.

The laser positioning mechanism may further comprise an actuator configured to move one or more components of the optical system to adjust the distance between said cutting laser beam and said skin contacting face of the device.

Movement of a component or components of the optical system will provide simple and accurate adjustment of the position of the cutting laser beam in the cutting zone.

Optionally, the one or more components is a reflective element configured to reflect a laser beam which forms the cutting laser beam.

Altering a reflection angle or position of a component can control the cutting height of the cutting laser beam without having to move a large assembly of components within the device. The actuator can be small, simple and lightweight.

In one embodiment, the optical system may comprise a first reflective element configured to reflect an incident laser beam across the cutting zone, and wherein the actuator is configured to move the first reflective element to adjust the distance between said cutting laser beam and said skin contacting face of the device.

In another embodiment, the optical system may comprise an additional reflective element which reflects a laser beam such that it is incident on said first reflective element, and wherein said actuator may be configured to move said additional reflective element to adjust the path of the incident laser beam which is incident on said first reflective element and thereby adjust the distance between the cutting laser beam and the skin contacting face.

In yet another embodiment, the optical system comprises an additional reflective element which reflects a laser beam such that it is incident on said first reflective element, and wherein said actuator is configured to move said additional reflective element to adjust the path of the incident laser beam which is incident on said first reflective element and thereby adjust the distance between the cutting laser beam and the skin contacting face.

Movement of the additional reflective element will alter the path of the reflected cutting laser beam and thereby alter the distance between the cutting laser beam and the skin contacting face. Only a small and simple movement of a relatively lightweight reflective element is required, which means only a small and lightweight actuator is required for this embodiment.

In a further embodiment the optical system further comprises two auxiliary reflective elements rotatably mounted on parallel axes, wherein said two auxiliary reflective elements are configured to reflect a laser beam onto said first reflective element and said actuator is configured to rotate said two auxiliary reflective elements to adjust the path of the incident laser beam which is incident on the first reflective element.

The actuator may be configured to move said first reflective element either along a path of the incident laser beam or along a path of the cutting laser beam in the cutting zone.

The control unit may be configured to adjust the intensity of the cutting laser beam in dependence on one or more of the optical properties detected by the skin sensor.

With this arrangement it is possible to reduce the effect, and therefore the irritation, potentially caused by the laser beam inadvertently being incident with the skin by changing the power or energy of the laser beam. This also means that it is possible to minimise the number of moving parts.

The skin sensor may be configured to detect one or more of the optical properties of the surface of the skin at an opening to the cutting zone.

This means that the skin sensor is able to detect the skin proximate to the cutting laser beam. Therefore, the skin sensor is able to detect properties of the skin at the area at which the laser beam is sited. Furthermore, the arrangement of the device is simplified because it is not necessary to provide another opening for the skin sensor.

The skin sensor may be received in a chamber defining the cutting zone. This means that the skin sensor is easily able to detect properties of the section of skin at the opening to the cutting zone. Dependent on the type of skin sensor, and/or the properties of the skin to be detected, it may be possible to use the cutting laser beam, or a section of the laser beam split off from the cutting laser beam, as a light source for the skin sensor.

Optionally the chamber has a reflective surface. With this arrangement light from a light source of the cutting element may be reflected in the chamber to maximise the detection of the properties of the skin at the opening to the cutting zone.

The skin sensor may be configured to sense the total reflectivity of the skin of a user when the device is in use.

With this arrangement the configuration of the skin sensor is minimised. For example, only one light source and one detector may be required.

The skin sensor may comprise a light source and a detector.

In one embodiment, the detector may be a broad band light source and the detector may be a broad band detector.

In another embodiment, the detector is a narrow band detector.

The light source may be the cutting laser, or the light source may be a beam split off from the cutting laser. With such an arrangement it is not necessary to provide a light source separate from the laser beam. Therefore, the device is simplified.

The skin sensor may be configured to detect the colour of the skin when the device is in use.

The device may further comprise a distance sensor configured to determine the distance between the cutting laser beam and the surface of the skin.

The control unit may be configured to reduce the intensity of the cutting laser beam when the distance detected between the cutting laser beam and the surface of the skin of a user falls below a minimum threshold value, wherein the minimum threshold value may be a function of the one or more of the optical properties of the skin detected by the skin sensor.

The control unit may be configured to change the distance between the cutting laser beam and the surface of the skin of a user in dependence on the distance detected by the distance sensor.

Therefore, a uniform cutting height can be maintained and variations in skin height can be accommodated by moving the cutting laser beam. In this way, skin doming and other skin height variations, such as skin contours, can be accommodated without reducing the performance of the device in terms of cutting height or skin irritation. Skin irritation will be reduced because the cutting laser beam will move in response to changes in the height of the skin in the cutting zone and so will not go within the predetermined distance of the skin and cause undue irritation. Said predetermined distance may be a function of one or more optical properties of the skin, as measured by the skin sensor.

Such a distance sensor as mentioned above may be used to change the power of the cutting laser beam as a function of the distance between the cutting laser beam and the surface of the skin. For example, the control unit may cease operation of the cutting laser beam when the detected distance becomes too small.

According to another embodiment, there is provided a system for cutting hair comprising a device for cutting hair according to any preceding claim and a base unit configured to receive the device, wherein the base unit comprises a calibration unit configured to calibrate the skin sensor to detect the optical properties of the surface of the skin.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
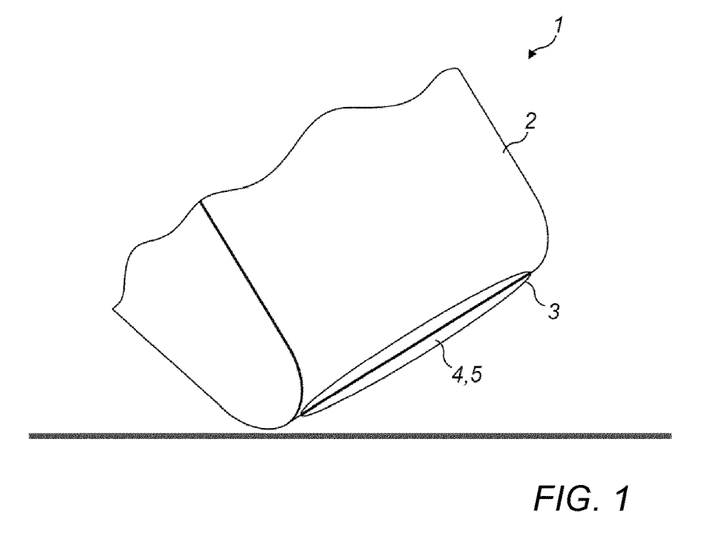
FIG. 1 shows a view of the cutting end of a device for cutting hair using a laser beam.
Figure 2:
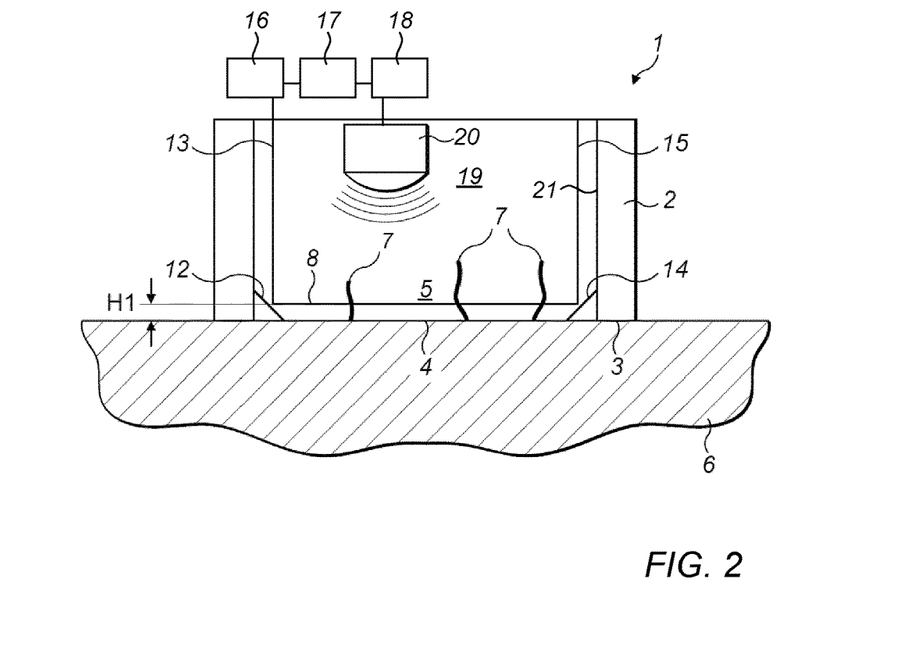
FIG. 2 shows a front view schematic diagram of the cutting end of the device of FIG. 1.

As shown in FIGS. 1 and 2, the device for cutting hair 1 comprises a main body 2 which includes a skin contacting face 3 having an opening 4. As shown in FIG. 2, during use, the skin contacting face 3 of the main body 2 is placed against the skin 6 of a user and hairs 7 on the skin 6 protrude into the opening 4 of the main body and into a cutting zone 5 defined therein. Within the opening 4 of the main body 2, the device 1 comprises an optical system which directs a cutting laser beam 8 across the cutting zone 5 so that the cutting laser beam 8 is parallel to and spaced from the skin contacting face 3 and opening 4 of the main body 2. In this way, when the skin contacting face 3 of the main body 2 is placed against the skin 6 of a user, the cutting laser beam 8 is substantially parallel to and spaced from the surface of the skin 6 of the user and provides a substantially uniform cutting height across the cutting zone 5. The distance between the surface of the skin 6 and the cutting laser beam 8 in the cutting zone 5, represented as distance H1 in FIG. 2, is the cutting height.

As shown in FIG. 2, the optical system generally comprises a first reflective element 12 positioned on one side of the opening 4 and cutting zone 5, which is configured to reflect an incident laser beam 13 across the opening 4 at the end of the device 1, across the cutting zone 5, such that the cutting laser beam 8 follows a path which is substantially parallel to and spaced from the skin contacting face 3 and opening 4 of the device 1. On an opposite side of the cutting zone 5 to the first reflective element 12, a second reflective element 14 is positioned to reflect the cutting laser beam 8 away from the cutting zone 5, towards an energy dissipater (not shown) so that the 'used' laser beam 15 is dissipated and can not interact with a part of the user or another part of the device. In the example shown in FIG. 2, the incident laser beam 13 which is incident on the first reflective element 12 is perpendicular to the skin contacting face 3 of the main body 2 and the first reflective element 12 reflects the laser beam through 90 degrees such that it is parallel to the skin contacting face 3 of the main body 2. Similarly, the second reflective element 14 is configured to reflect the cutting laser beam 8 through 90 degrees and perpendicularly away from the cutting zone 5 back towards the main body 2 of the device 1. However, it will be appreciated that the first and second reflective elements 12, 14 may be orientated differently or have different reflective angles, depending on the position and orientation of other parts of the optical system, such as a laser beam generator 16 and an energy dissipater (not shown). Furthermore, it will be appreciated that the first and second reflective elements 12, 14 may not be located at a side of the cutting zone 5. They may alternatively be located anywhere within the cutting zone 5, depending on the position, orientation and configuration of the other components of the optical system. However, the cutting laser beam 8 within the cutting zone 5 should remain parallel to the skin contacting face 3 and opening 4 of the main body 2 so that the distance between the skin contacting face 3 and the cutting laser beam 8 is constant across the cutting zone 5.

The optical system of the device 1 further comprises the laser generator 16, such as a diode, and a laser driver 17. The device 1 also comprises a control unit 18, also known as a controller. The control unit 18 is configured to control operation of the laser driver 17 and laser generator 16, and so control operation of the cutting laser beam 8. Other components that the device 1 may comprise, which are not shown, may include other optical components such as a collimating lens or filter. Other components necessary for the operation of the device may also be located within the main body 2, such as a battery or a connection to an external power cable. Moreover, the main body 2 of the device may also comprise a handle and any switches, buttons or other controls and displays necessary to operate the device. Any reflective elements described herein may comprise a mirror or a prism or any other optically reflective surface.

The cutting zone 5 is formed in a chamber 19 in the main body 2. The opening 4 to the cutting zone 5 is defined by an opening to the chamber 19.

The device 1 is provided with a skin sensor 20. The skin sensor 20 is an electronic sensor which determines one or more optical properties of the skin 6 when the device 1 is positioned against the skin 6. That information is provided to the control unit which controls operation of the laser driver 17 and laser generator 18.

The skin sensor 20 is configured to detect one or more optical properties of the skin 6. In particular, the skin sensor 20 is configured to detect one or more optical properties of a section of the skin 6 disposed at the opening 4 to the cutting zone 5. An advantage of this arrangement is that the skin sensor 20 is able to determine the optical properties of the skin 6 adjacent to the cutting laser beam 8. The skin sensor 20 is disposed in the cutting zone 5. That is, in the present arrangement the skin sensor 20 is disposed in the chamber 19 in the main body 2.

The skin sensor 20 is a non-contact skin colour sensor. That is, the skin sensor 20 is configured to measure the colour of the skin. The skin sensor 20 may be a reflective or transmissive optical sensor. The skin sensor 20 may use one or more wavelengths of light in the visible and/or near infra-red radiation regions. However, it will be understood that alternative sensor arrangements may be used.

The skin sensor 20 comprises a light source (not shown) and a detector (not shown). A light path is defined between the light source and the detector. A user's skin forms part of the light path when the skin 6 is disposed at the opening 4 to the cutting zone 5. The skin sensor 20 is configured to detect the optical absorption level of the skin, such that the skin melanin contributes to the absorption signal.

In the present embodiment the skin sensor 20 uses a wavelength of 700 nm. However, alternative wavelengths may be used. In one embodiment the skin sensor uses two or more different wavelengths to determine the one or more optical properties of the skin 6. In such an arrangement the detector of the skin sensor 20 comprises detector elements which are configured to detect each of the different wavelengths. By using a sensor which is able to determine two or more wavelengths, the colour of the skin can be determined by measuring the relative absorption signal at each wavelength. An advantage of this arrangement is that it is not necessary to measure the absolute absorption.

In another embodiment, the skin sensor 20 is configured to measure the total absolute reflectivity of the skin 6 at the opening 4 to the cutting zone 5. With this arrangement the skin sensor 20 comprises the light source (not shown) and the detector (not shown). An advantage of the skin sensor measuring the total absolute reflectivity of the skin 6 is that the arrangement of the skin sensor 20 may be simplified. For example, the skin sensor 20 may have one single light source and one single detector element.

In such an embodiment, the light source (not shown) of the sensor 20 is a broad band light source, for example a light source emitting a white light, and the detector of the sensor 20 is a broad band detector. Alternatively, the light source of the sensor 20 is a narrow band light source, for example a light emitting diode (LED), and the detector of the sensor 20 is a corresponding narrow band detector. However, it will be appreciated that alternative arrangements are envisaged. For example, in one embodiment the light source of the sensor 20 is formed by the cutting laser beam 8. Alternatively, the light source of the sensor 20 is formed by a portion of the laser beam forming the cutting laser beam 8. In such an arrangement the portion of the laser beam forming the light source of the sensor 20 is split off from the laser beam forming the cutting laser beam 8.

The skin sensor 20 is provided in the chamber 19. When the skin 6 of a user is disposed at the opening 4, the chamber 19 is enclosed. Therefore, the light reflected from the skin 6 of the user is reflected within the chamber prior to being guided to the detector or each detector of the sensor 20. An inner surface 21 of the chamber 19 is coated with a reflective coating. That is, the inner surface 21 of the chamber 19 is a reflective surface. For example, in an embodiment with a light source emitting a white light, the inner surface 21 is a white reflective surface.

In one embodiment a guard (not shown) is provided over the opening 4. The guard acts to prevent the cutting laser beam 8 from being directed out through the opening 4. Furthermore, the guard may restrict the skin 6 of a user from being inserted through the opening 4. Apertures are provided in the guard to allow hairs 7, upstanding from the skin 6, to protrude through the opening 4 to intersect the cutting laser beam 8. Skin contact sensors (not shown) determine when the device 1 is in contact with the skin 6 of the user.

Although in the present arrangement the skin sensor 20 is disposed in the cutting zone 5 and is configured to detect the optical properties of the skin 6 positioned at the opening 4 to the cutting zone 5, it will be understood that in an alternative embodiment the skin sensor 20 may be disposed outside the cutting zone 5. For example, the skin sensor 20 may be disposed to detect skin at a sensor opening (not shown) adjacent to the opening 4 to the cutting zone 5.

A base unit (not shown) is provided. The base unit is configured to receive the device 1. The base unit and the device 1 together form a system for cutting hair. The base unit may be configured to support the device 1. In one embodiment the base unit has a power supply and a charging unit for charging the device 1. Therefore, the device 1 may be a cordless device.

The base unit (not shown) has a support to hold the lower end of the main body 2. The opening 4 to the cutting zone 5 is provided in the lower end of the main body 2. The base unit has a calibration unit (not shown). The calibration unit (not shown) is configured to calibrate the skin sensor 20.

The calibration unit comprises a reference surface (not shown). The reference surface is configured to have a reference colour, that is, a surface having a reference reflectivity value. In one embodiment the reference surface is white. Therefore, the calibration unit is able to calibrate the skin sensor 20.

When the device 1 is disposed on the base unit, the opening 4 to the cutting zone 5 is disposed against the reference surface of the calibration unit. Therefore, the control unit 18 is configured to operate the sensor 20 in a calibration mode to calibrate the sensor 20. The device 1 may be operable in the calibration mode when the device 1 is placed on the base unit, or in response to a user input. The calibration unit ensures that the correct adjustment of one or more characteristics of the optical system in dependence on one or more of the optical properties of the skin detected by the skin sensor is made when the device is used. Therefore, the sensor 20 is able to provide an accurate reading despite any changes to, for example, the chamber 19 or sensor 20 after use or prolonged use of the device 1, such as dirt and detritus being received in the chamber 19.

When the device 1 is operated, the control unit 18 is configured to adjust one or more characteristics of the optical system in dependence on one or more of the optical properties of the skin 6 detected by the skin sensor 20. The skin sensor 20 is operable to detect one or more optical properties of the skin 6 of the user, for example the colour or total reflectivity, as discussed above.

In one embodiment, dependent on the optical properties detected by the skin sensor 20, the control unit 18 is operable to adjust the intensity of the cutting laser beam 8. With such an arrangement, the control unit 18 operates the laser generator 16 to adjust the intensity of the cutting laser beam 8, for example the power or energy of the laser beam emitted by the laser generator 16, dependent on the skin type detected. The control unit 18, for example, refers to a look-up table stored on a storage device, for example solid state memory, to determine the correct laser beam intensity, or alternatively the control unit is configured to calculate the correct laser intensity. For example, the control unit 18 is configured to reduce by about a factor of three when the skin type detected by the skin sensor 20 changes from a type II skin on the Fitzpatrick scale to a type IV skin on the Fitzpatrick scale. That is, the laser intensity set by the control unit 18 for a lower skin type on the Fitzpatrick skin type scale is configured to be higher than the laser intensity set by the control unit 18 for a higher skin type on the Fitzpatrick skin type scale, and so the laser intensity is reduced if a higher skin type on the Fitzpatrick skin type scale is detected by the skin sensor 20.

In another embodiment, the device also comprises a skin distance sensor (not shown). However, it will be understood that the skin distance sensor (not shown) may be omitted. The skin distance sensor may be an inductive sensor, such as a displacement potentiometer which has a sprung arm which extends to contact the skin 6. Alternatively, the skin detector may be an optical sensor, such as a confocal lens which uses optical measuring techniques and does not need to contact the skin to measure the distance between the surface of the skin a reference point on the device 1. The control unit 18 is configured to adjust the intensity of the cutting laser beam 8 dependent on changes in the height of the skin 6 of a user within the cutting zone 5, for example due to skin height variations and the skin doming in the cutting zone 5. That is, the device is configured to reduce the intensity of the cutting laser beam 8, for example the power or the energy of the laser beam, when the distance detected between the cutting laser beam 8 and the surface of the skin 6 of the user by the skin distance sensor falls below a minimum threshold value. In this way, skin doming and other skin height variations, such as skin contours, can be accommodated whilst reducing skin irritation.

When a device 1, such as that shown in FIGS. 1 and 2, is placed against the skin 6 of a user there is a minimum threshold value of distance between the surface of the skin 6 and the cutting laser beam 8. When the device 1 is operated, the control unit 18 is configured to reduce the cutting laser beam 8 intensity when the distance between the surface of the skin 6 and the cutting laser beam 8 detected by the skin distance sensor falls below the minimum threshold value.

The control unit 18 is configured to adjust the minimum threshold value of distance between the surface of the skin 6 and the cutting laser beam 8 dependent on the optical properties, for example total skin reflectivity, detected by the skin sensor 20. Therefore, the minimum threshold value of distance set by the control unit 18 between the surface of the skin 6 and the cutting laser beam 8 for a lower skin type on the Fitzpatrick scale is less than the minimum threshold value of distance between the surface of the skin 6 and the cutting laser beam 8 for a higher skin type on the Fitzpatrick scale.

The minimum threshold value for the distance may be determined by the control unit dependent on the optical properties detected by the skin sensor 20, for example, by reference to a look up table stored by a storage device (not shown).

Although in the above embodiment the control unit 18 is configured to adjust one or more characteristics of the optical system by adjusting the intensity of the cutting laser beam 8, it will be understood that other characteristics of the optical system may be adjusted.

In an alternative embodiment, the device is configured to move the cutting laser beam 8 in a direction perpendicular to the longitudinal direction of the cutting laser beam 8 in the cutting zone 5, towards or away from the opening 4 and skin contacting face 3 of the main body 2, in response to one or more of the optical properties of the skin 6 detected by the skin sensor 20. An advantage of this arrangement is that the intensity of the cutting laser beam 8 does not change dependent on the optical properties of the skin 6 detected by the skin sensor 20.

Movement of the cutting laser beam 8 in response to one or more of the optical properties of the skin 6 detected by the skin sensor 20 will help to reduce, and may eliminate, the negative effects that differences in skin type causes for the quality and effectiveness of shaving. In particular, the device is able to move the cutting laser beam 8 to adjust for differences in skin type and so avoiding undue interaction between the cutting laser beam 8 and the skin 6 of a user being incident with the cutting laser beam 8.

It will be appreciated that moving the cutting laser beam 8 in response to one or more of the optical properties of the skin 6 detected by the skin sensor 20 will allow the device to generally maintain shaving performance regardless of the skin type received within the cutting zone 6.

Figure 3:
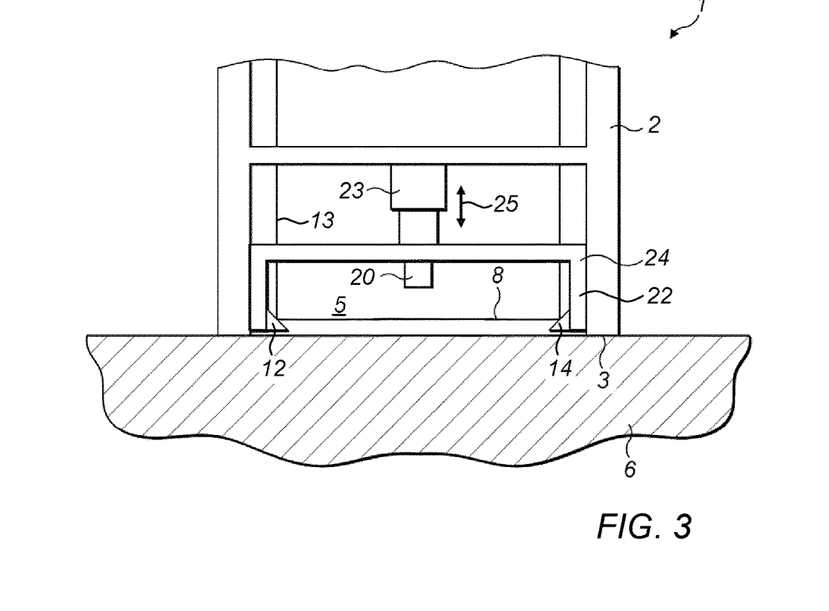
FIG. 3 shows a front view schematic diagram of another embodiment of the cutting end of the device of FIG. 1.

FIG. 3 shows an embodiment of a device 1 for cutting hair which includes a main body 2, as previously described with reference to FIGS. 1 and 2, which comprises an opening 4 at one end and a skin contacting face 3 which is configured to contact the skin 6 during use of the device. Moreover, the skin contacting face 3 may be provided with leading and trailing edge stretchers (not shown) to pull the skin 6 within the cutting zone 5 so that features of the skin 6 are smoothed out. This minimises variations in skin height.

As shown in FIG. 3, the device 1 is also provided with a laser positioning mechanism 22. The laser positioning mechanism 22 has a frame 24 that is moveably mounted within the main body 2 such that it is able to move towards and away from the skin contacting face 3 of the main body 2 in the direction of arrow 25. One or more components of the optical system are also mounted to the frame 24; in this example, the first and second reflective elements 12, 14 are positioned on the frame 16 to reflect an incident laser beam 13 across the cutting zone 5 to create a cutting laser beam 8, as previously explained. Movement of the frame 24 towards and away from the skin contacting face 3 of the main body 2 will vary the effective cutting height, as desired.

To achieve the desired movement of the cutting laser beam 8, in the direction of arrow 25, the frame 24 may be telescopically mounted within the main body 2 and that mounting may include linear slide bearings, rails or another connection that allows the frame 24 to slide relative to the main body 2. In this case, the frame 24 is mounted such that it can move in a direction parallel to the incident laser beam 13 which is incident on the first reflective element 12. This movement is therefore perpendicular to the longitudinal direction of the cutting laser beam 8 within the cutting zone 5 and so the movement of the frame 24 will not effect the arrangement of the optical system, so that the incident laser beam 13 will still be reflected across the cutting zone 5 to form a cutting laser beam 8 which is parallel to the skin contacting face 3 of the device 1.

The frame 24 is configured to move along linear rails which define a path which is perpendicular to the plane of the opening 4 and skin contacting face 3 of the main body 2. That is, the frame 24 moves along the path of the incident laser beam 13 which is incident on the first reflective element 12. However, it will be appreciated that this movement may alternatively be at a non-perpendicular angle to the skin contacting face 3.

The moveable frame 24 is mounted on an actuator 23 which is configured to move the frame 24. The device may include one or more actuators that control the position of the frame 24 within the device. For example, FIG. 3 shows a single, centrally located actuator 23 but this may be substituted with two spaced actuators acting synchronously. The actuator 23 forms part of the laser positioning mechanism 22. Movement of the laser positioning mechanism 22 causes movement of the cutting laser beam 8 in a linear direction towards and away from the skin contacting face 3 of the main body 2 and therefore the skin 6 of the user during use. The actuator 23 may be an electronic actuator, for example a voice coil actuator, which moves the frame 24 in response to commands from the control unit 18.

The device 1 has a skin sensor 20, as previously described. The skin sensor 20 is in the chamber 19 defining the cutting zone 5. In the present embodiment the skin sensor 20 is on the frame 24, although it will be understood that the skin sensor 20 may be mounted elsewhere. The skin sensor 20, determines one or more optical properties of the skin 6 of the user, as previously described. That information is provided to the control unit 18 which controls the position of the actuator 23, which is configured to move the frame 24 and cutting laser beam 8 in response to the determined one or more optical properties of the skin 6.

When the device shown in FIG. 3 is placed against the skin 6 of a user there is a minimum threshold value of distance between the surface of the skin 6 and the cutting laser beam 8. That is, the control unit 18 is configured to control the laser positioning mechanism 22 so that the distance between the cutting laser beam 8 and the skin contacting face 3 is adjusted dependent on the optical properties, for example total skin reflectivity, detected by the skin sensor 20. When the device 1 is operated the control unit 18 is configured to operate the actuator 23 of the laser positioning mechanism 22 to adjust the minimum distance between the surface of the skin 6 and the cutting laser beam 8 dependent on the optical properties detected by the skin sensor 20. Therefore, the distance set by the control unit 18 between the cutting laser beam 8 and the skin contacting face 3 for a lower skin type on the Fitzpatrick scale is less than the distance between the surface of the skin 6 and the cutting laser beam 8 for a higher skin type on the Fitzpatrick scale.

The distance set by the control unit 18 between the cutting laser beam 8 and the skin contacting face 3 may be determined by the control unit 18, for example, by reference to a look up table stored by a storage device (not shown).

The device 1 also comprises a skin distance sensor (not shown). However, it will be understood that the skin distance sensor (not shown) may be omitted. The skin distance sensor may be an inductive sensor, such as a displacement potentiometer which has a sprung arm which extends to contact the skin 6. Alternatively, the skin detector may be an optical sensor, such as a confocal lens which uses optical measuring techniques and does not need to contact the skin to measure the distance between the surface of the skin a reference point on the device 1. The control unit 18 is configured to move the cutting laser beam 8 in a direction perpendicular to the longitudinal direction of the cutting laser beam 8 in the cutting zone 5 to maintain a minimum value of distance H1 between the surface of the skin 6 and the cutting laser beam 8 dependent on changes in the height of the skin 6 of a user within the cutting zone 5, for example due to skin height variations and the skin doming in the cutting zone 5. That is, the device is configured to maintain a consistent effective cutting height in response to changes in the skin height in the cutting zone 5 during use.

Alternatively, in an embodiment not shown in the drawings, a laser generator may be mounted to the cutting head frame which is rotatably mounted, such that the laser beam is moved away or towards the end opening and therefore the skin of the user. As the laser beam generator is also mounted to the rotatable frame the relative arrangement of the laser beam generator and the first reflective element is not affected by the rotation so the laser beam will still be reflected across the cutting zone such that it is parallel to the skin contacting face of the device.

Figure 4:
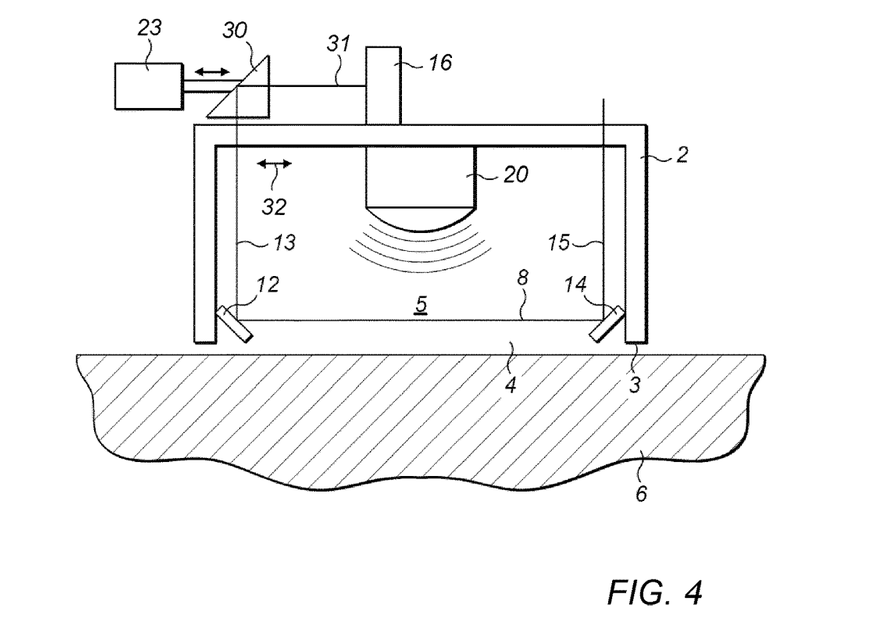
FIG. 4 shows a front view schematic diagram of a further embodiment of the cutting end of the device of FIG. 1.
Figure 5:
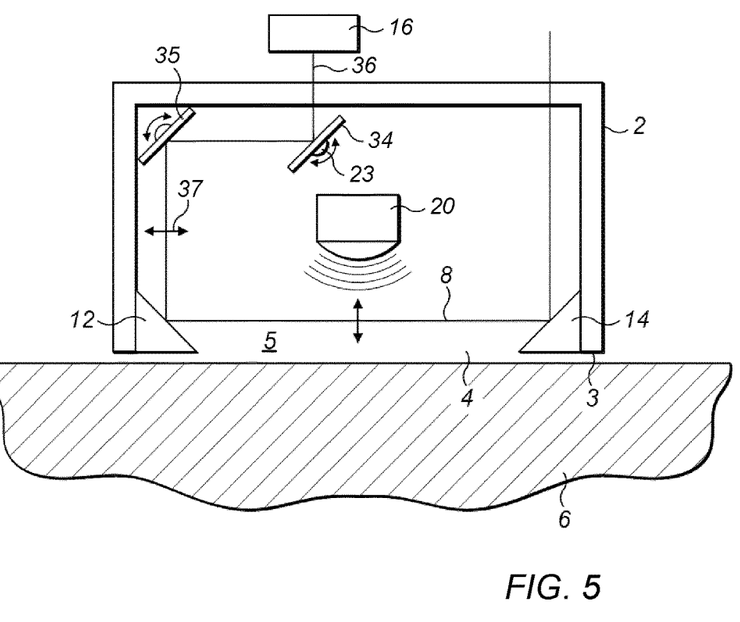
FIG. 5 shows a front view schematic diagram of a different embodiment of the cutting end of the device of FIG. 1.
Figure 6:
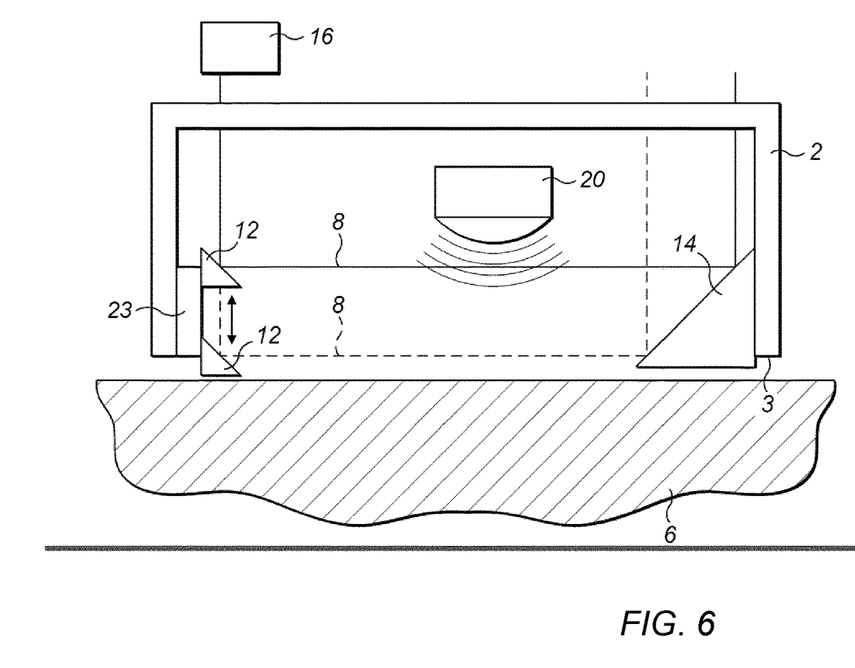
FIG. 6 shows a front view schematic diagram of another embodiment of the cutting end of the device of FIG. 1.

Further embodiments are shown in FIGS. 4 to 6. These embodiments also comprise a main body 2 having a skin contacting face 3 and an opening 4 which are pressed against the skin 6 of a user during use. However, the laser positioning mechanisms 22 of these embodiments do not comprise a moveable frame as described with reference to FIG. 3. Instead, the cutting laser beam 8 is moved by an actuator 23 which in configured to move a component of the optical system, as will be explained below. Each of the embodiments shown in FIGS. 4 to 6 has a skin sensor 20 configured to determine the one or more optical properties of the skin 6 as described above.

To move the cutting laser beam 8 in response to the one or more optical properties of the skin 6, as determined by the skin sensor 20, the device 1 includes a control unit (not shown in FIGS. 4 to 6) and an actuator 23 to move the cutting laser beam 8 by moving a component of the optical system.

The embodiment shown in FIG. 4 includes a skin sensor 20 to determine the one or more optical properties of the skin 6 of a user. The device 1 also comprises first and second reflective elements 12, 14 positioned either side of the cutting zone 5, as described previously, to reflect an incident laser beam 13 first through 90 degrees and across the cutting zone 5 and subsequently through another 90 degrees and away towards an energy dissipater (not shown). This embodiment also includes a third reflective element 30 and an actuator 23 which is configured to move the third reflective element 30 relative to the main body 2 of the device 1 to alter the path of the incident laser beam 13 which is incident on the first reflective element 12. For example, as shown in FIG. 4, a laser generator 16 is disposed to emit a laser beam 31 in a direction parallel to the cutting laser beam 8 and the third reflective element 30 is disposed to reflect that laser beam 31 through 90 degrees and towards the first reflective element 12. The third reflective element 30 is configured to move, under influence of the actuator 23, either towards or away from the laser generator 16 along the path of the laser beam 31 emitted by the generator 16. In this way, the path of the incident laser beam 13 which is incident on the first reflective element 12 is moved in the direction of arrow 32, which changes the point of reflection on the first reflective element 12 and thereby adjusts the distance between the cutting laser beam 8 and the skin contacting face 3 of the main body 2. Therefore, the distance between the skin contacting face 3 and the cutting laser beam 8 can be controlled by the control unit, via the actuator 23, in response to the detected one or more optical properties of the skin 6 of the user. In this way, the effective cutting height can be adjusted in response to the determined one or more optical properties of the skin 6 of the user.

The actuator 23 configured to move the third reflective element 30 may be a voice coil actuator or any other type of suitable controllable actuator. The third reflective element 30 may be mounted on a slide rail or guide to control the path along which it moves or the actuator 23 may have a built in guide. It will also be appreciated that the arrangement shown in FIG. 4, with each of the reflective elements 12, 14, 30 being configured to reflect the laser beam through 90 degrees, may be altered by changing the orientation of the optical components and reflective angles of the reflective elements.

The embodiment of FIG. 4 shows an actuator 23 configured to move a third reflective element 12 along a path parallel to the cutting laser beam 8. However, it will be appreciated that an alternative embodiment of the invention would be to provide an actuator that is configured to move the laser beam generator along a path parallel to the cutting laser beam, whereby the laser beam generator emits a laser beam directly towards the first reflective element 12. In this way, the height of the cutting laser beam 8 in the cutting zone 5 is adjusted.

In another embodiment, shown in FIG. 5, a galvanometer mirror arrangement is used to control the position of the incident laser beam 13 which is incident on the first reflective element 12, and therefore control the height of the cutting laser beam 8 in the cutting zone 5. In the example shown in FIG. 5, the galvanometer mirror arrangement comprises two mirrors 34, 35 which are independently rotatable about parallel axes by means of at least one actuator 23, such that the direction of the incident laser beam 13 is controllable by altering the rotational positions of the two mirrors 34, 35. A laser beam 36 from a laser generator 16 is incident on the first rotatable mirror 34 which reflects the laser beam towards the second rotational mirror 35 which in turn reflects the incident laser beam 13 towards the first reflective element 12 and subsequently into the cutting zone 5. In this way, by controlling the rotational position of the mirrors 34, 35 in response to the determined one or more optical properties of the skin 6 of the user, as determined by the skin sensor 20, the incident laser beam 13 which is incident on the first reflective element 12 can be moved in the direction of arrow 37 along a direction perpendicular to its longitudinal axis, thereby controlling the height of the cutting laser beam 8 in the cutting zone 5.

It will be appreciated that other optomechatronic mechanisms may be used in place of the galvanometer mirror arrangement to control the position of the cutting laser beam 8 in the cutting zone 5.

In another embodiment, shown in FIG. 6, the first reflective element 12, which is positioned to one side of the cutting zone 5, is mounted on an actuator 23 configured to move the first reflective element 12 towards or away from the skin contacting face 3 of the main body 2 along the path of the incident laser beam 13. In this way, the cutting laser beam 8 in the cutting zone 5 is moved to control the effective cutting height.

Similarly to the embodiments described with reference to FIGS. 4 and 5, the device will comprise a skin sensor 20 to determine the one or more optical properties of the skin 6 of a user and this skin sensor 20 may be the same as any of the previously described sensors. The actuator 23 may be a voice coil type actuator which is configured to move the first reflective element 12 in a linear direction along the same path as the incident laser beam 13 from a laser generator 16 such that the incident angle is not altered. The first reflective element 12 is configured to reflect the incident laser beam 13 at a right angle, across the cutting zone 5, such that it is parallel to the skin contacting face 3 of the main body 2. In this way, as the first reflective element 12 is moved along the path of the incident laser beam 13 the reflected cutting laser beam 8 in the cutting zone 5 is moved to alter the height of the cutting laser beam 8 in the cutting zone 5 and thereby adjust the effective cutting height. The second reflective element 14 may be mounted on a separate actuator or connected to the actuator 23 of the first reflective element 12 such that both move synchronously.

Alternatively, as shown in FIG. 6, the second reflective element 12 may be fixed, in this case the second reflective element 12 should extend far enough to ensure that the cutting laser beam 8 from the cutting zone 5 is incident on the second reflective element 14 at any position of the first reflective element 12 and height of the cutting laser beam 8 in the cutting zone 5. For example, as shown in FIG. 6, the first reflective element 12 is mounted on an actuator 23 that moves the first reflective element 12 along the path of the incident laser beam 13 and the second reflective element 14 is fixed and is larger, extending further than the first reflective element 12 such that even at the extreme positions of the first reflective element 12 the cutting laser beam 8 from the cutting zone 5 is still incident on the second reflective element 14.

The embodiment of FIG. 6 shows an actuator 23 configured to move the first reflective element 12 along a path parallel to the incident laser beam 13, and perpendicular to the cutting laser beam 8. However, it will be appreciated that an alternative embodiment of the invention would be to provide the first reflective element 12 with an actuator that moves the first reflective element 12 along a path parallel to the cutting laser beam 8, into the cutting zone 5. In this way, the height of the cutting laser beam 8 in the cutting zone 5 is adjusted.

Although each of the embodiments of the invention described above with reference to FIGS. 3 to 6 move the laser beam in such a way as the laser beam remains parallel to the skin contacting face of the device, it will be appreciated that the moveable frame, actuator and/or optical system may be configured to move the laser beam in such a way that it does not remain parallel to the skin contacting face of the device. For example, the frame may be able to rotate as well as slide in response to changes in the height of the skin in the cutting zone. Alternatively, the optical system may be provided with an optomechatronic system that acts in response to multiple skin height sensors positioned across the cutting zone to change the height and angle of the laser beam.

In the embodiments described above, the second reflective element is configured to reflect the laser beam from the cutting zone towards an energy dissipater which dissipates the laser beam and prevents any further damage being caused by the laser beam. However, it will be appreciated that the second reflective element may instead be configured to reflect the laser beam back across the cutting zone, parallel to and spaced from the first laser beam in the cutting zone and thereby create a multi-beam cutting action. This may be repeated multiple times. A subsequent reflective element may reflect the laser beam towards an energy dissipater after the laser beam has passed across the cutting zone a number of times.

In each of the above embodiments the one or more characteristics of the optical system that are adjusted in dependence on one or more of the optical properties of the skin detected by the skin sensor may be adjusted dynamically as the device 1 is moved over the skin 6 of a user dependent on the specific optical properties of the skin. An advantage of this arrangement is that the device is able to dynamically adjust operation of the cutting laser beam 8 to each part of a user's skin. Alternatively, the control unit 18 may be configured to determine the optical properties of the skin 6 upon the device being placed against the skin 6, or at a predetermined stage. An advantage of this arrangement is that a consistent operation of the device 1 is obtained.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for cutting hair comprising:
   a chamber provided with a skin contacting face that is arranged to be placed against a surface of skin of a user during use;
   an optical system that comprises at least a laser generator that generates a cutting laser beam and reflective elements, wherein the optical system directs the cutting laser beam, via the reflective elements, across a cutting zone in the chamber parallel to and spaced from said skin contacting face to cut hairs extending through an opening in said skin contacting face of the chamber into the cutting zone;
   a skin sensor that detects one or more optical properties of the surface of the skin disposed at the opening in the skin contacting surface of the chamber, wherein the one or more optical properties includes colour for use in identifying different skin types, from a lower skin type to a higher skin type, that consist of one of six types between Type I which is identified as light, pale white and Type VI which is identified as black, very dark brown to black;
   a skin distance sensor that comprises at least one of an inductive sensor, a displacement potentiometer with a sprung arm to contact the skin, and an optical sensor, wherein the skin distance sensor is configured to measure a distance between the surface of the skin disposed at the opening in the skin contacting surface of the chamber and a reference point on the device, wherein the measured distance is representative of a height of the skin above the skin contact surface of the chamber within the cutting zone; and
   a controller operatively coupled to at least the laser generator of the optical system, the skin sensor and the skin distance sensor, wherein the controller adjusts one or more characteristics of the optical system in response to the one or more of the optical properties of the skin detected by the skin sensor, via at least controlling the laser generator to generate the cutting laser beam with (i) an increased laser intensity in response to a lower skin type detected via the skin detector and (ii) a reduced laser intensity in response to a higher skin type detected via the skin detector, wherein the controller further adjusts the one or more characteristics of the optical system in response to the distance measured by the skin distance sensor, via at least controlling an actuator of a laser positioning mechanism that is mechanically coupled to one or more of the reflective elements to increase a distance between the cutting laser beam and the surface of the skin within the cutting zone in response to a difference between a height of the cutting laser beam and the height of the skin within the cutting zone falling below a minimum threshold value, further wherein the controller adjusts the minimum threshold value in response to the one or more of the optical properties of the skin detected by the skin sensor, via (i) a first minimum threshold value for the lower skin type and (ii) a second minimum threshold value for the higher skin type, wherein the first minimum threshold value is less than the second minimum threshold value, and thereby dynamically adjusts an operation of the cutting laser beam.

2. The device for cutting hair according to claim 1, wherein the controller further adjusts a distance between the cutting laser beam and the skin contacting face, via controlling the actuator of the laser positioning mechanism that is mechanically coupled to the one or more reflective element of the reflective elements to move the one or more reflective element and thereby move the cutting laser beam in a direction perpendicular to a longitudinal direction of the cutting laser beam in the cutting zone, towards or away from the opening and the skin contacting surface of the chamber, in response to the one or more optical properties of the skin detected by the skin sensor.

3. The device for cutting hair according to claim 1, wherein the skin sensor is received in the chamber defining the cutting zone, wherein the chamber includes a reflective surface.

4. The device for cutting hair according to claim 1, wherein the skin sensor is configured to sense a total reflectivity of the skin of a user disposed at the opening in the skin contacting surface of the chamber when the device is in use.

5. The device for cutting hair according to claim 4, wherein the skin sensor comprises a light source and a detector, wherein the light source is a broad band light source and the detector is a broad band detector.

6. The device for cutting hair according to claim 4, wherein the skin sensor comprises a light source and a detector, wherein the light source comprises one selected from the group consisting of a narrow band light source, a cutting laser, and a beam split off from the cutting laser.

7. A system for cutting hair comprising a device for cutting hair according to claim 1 and a base unit configured to receive the device, wherein the base unit comprises a calibration unit provided with a reference surface and configured to calibrate the skin sensor, via the reference surface, to detect the optical properties of the surface of the skin of a user.

* * * * *